United States Patent
Foley et al.

(10) Patent No.: US 8,591,555 B2
(45) Date of Patent: Nov. 26, 2013

(54) SYSTEM WITH INTEGRAL LOCKING MECHANISM

(75) Inventors: Kevin Foley, Germantown, TN (US); Newt Metcalf, Memphis, TN (US); Greg Marik, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 484 days.

(21) Appl. No.: 12/551,152

(22) Filed: Aug. 31, 2009

(65) Prior Publication Data

US 2011/0054542 A1    Mar. 3, 2011

(51) Int. Cl.
*A61B 17/80*    (2006.01)

(52) U.S. Cl.
USPC .......................................................... 606/289

(58) Field of Classification Search
USPC ............. 606/280–299, 70, 71, 307, 308, 309, 606/254–256
See application file for complete search history.

(56) References Cited

U.S. PATENT DOCUMENTS

| | | | |
|---|---|---|---|
| 5,616,142 A * | 4/1997 | Yuan et al. ....................... | 606/71 |
| 6,030,389 A | 2/2000 | Wagner et al. | |
| 6,224,602 B1 * | 5/2001 | Hayes ............................. | 606/296 |
| 6,258,089 B1 | 7/2001 | Campbell et al. | |
| 6,398,783 B1 | 6/2002 | Michelson | |
| 6,602,256 B1 * | 8/2003 | Hayes ............................. | 606/296 |
| 6,605,090 B1 | 8/2003 | Trieu et al. | |
| 6,626,907 B2 | 9/2003 | Campbell et al. | |
| 6,733,531 B1 * | 5/2004 | Trieu ........................... | 623/17.11 |
| 7,025,769 B1 | 4/2006 | Ferree | |
| 7,166,109 B2 * | 1/2007 | Biedermann et al. ......... | 606/279 |
| 7,169,150 B2 * | 1/2007 | Shipp et al. .................... | 606/287 |
| 7,481,811 B2 | 1/2009 | Suh | |
| 2001/0041894 A1 | 11/2001 | Campbell et al. | |
| 2004/0030338 A1 | 2/2004 | Paul | |
| 2004/0300338 | 2/2004 | Paul | |
| 2004/0210217 A1 | 10/2004 | Baynham et al. | |
| 2005/0137597 A1 * | 6/2005 | Butler et al. .................... | 606/69 |
| 2005/0177157 A1 * | 8/2005 | Jahng .............................. | 606/61 |
| 2005/0187554 A1 * | 8/2005 | Michelson ...................... | 606/70 |
| 2005/0261690 A1 * | 11/2005 | Binder et al. ................... | 606/69 |
| 2006/0085001 A1 * | 4/2006 | Michelson ...................... | 606/69 |
| 2006/0122604 A1 | 6/2006 | Gorhan et al. | |
| 2006/0149253 A1 | 7/2006 | Doubler et al. | |
| 2006/0200147 A1 | 9/2006 | Ensign et al. | |
| 2006/0247639 A1 * | 11/2006 | Anderson ....................... | 606/69 |
| 2006/0276794 A1 * | 12/2006 | Stern .............................. | 606/69 |
| 2006/0293673 A1 * | 12/2006 | Morrison et al. ............... | 606/69 |
| 2007/0073297 A1 | 3/2007 | Reynolds | |
| 2007/0156143 A1 * | 7/2007 | Lancial ........................... | 606/61 |
| 2007/0233117 A1 * | 10/2007 | Butler et al. .................... | 606/69 |
| 2007/0239158 A1 * | 10/2007 | Trieu et al. ..................... | 606/69 |
| 2008/0161854 A1 * | 7/2008 | Bae et al. ....................... | 606/246 |

(Continued)

OTHER PUBLICATIONS

International Search Report mailed on Mar. 31, 2011.

*Primary Examiner* — Andrew Yang
*Assistant Examiner* — Diana S Jones

(57) ABSTRACT

A system for affixing at least two portions of bone is provided. The system has a first end cap, a second end cap, and a linking member extending between the first end cap and the second end cap. The first end cap has at least one leg configured to connect the linking member to the first end cap and configured to retain the connection. The system provides an integral locking system mechanism that does not require an additional locking element.

20 Claims, 13 Drawing Sheets

(56) References Cited

U.S. PATENT DOCUMENTS

| | | |
|---|---|---|
| 2008/0161862 A1 | 7/2008 | Ensign |
| 2008/0243192 A1 | 10/2008 | Jacene et al. |
| 2008/0269804 A1* | 10/2008 | Holt .............................. 606/254 |
| 2009/0024170 A1 | 1/2009 | Kirschman |
| 2009/0036933 A1 | 2/2009 | Dube et al. |
| 2009/0062862 A1 | 3/2009 | Perrow et al. |
| 2009/0088808 A1 | 4/2009 | Lindemann et al. |
| 2009/0171397 A1 | 7/2009 | Rothman et al. |

* cited by examiner (DRAWN TO SCALE)

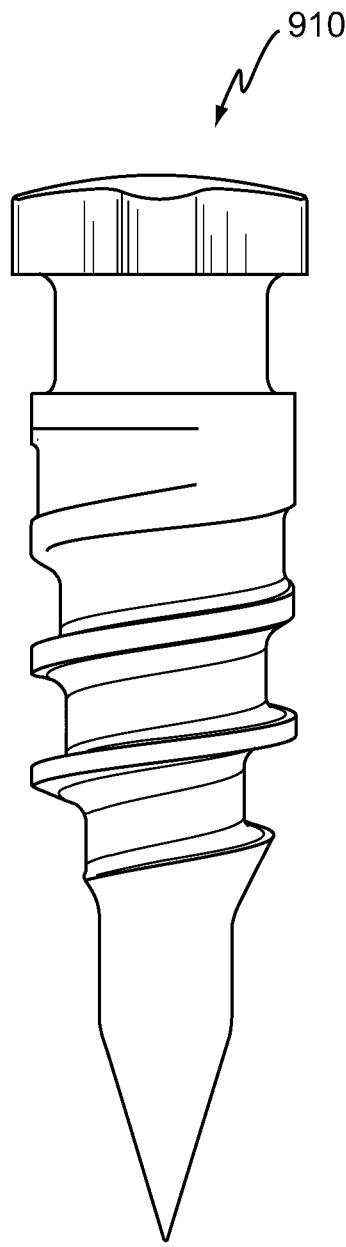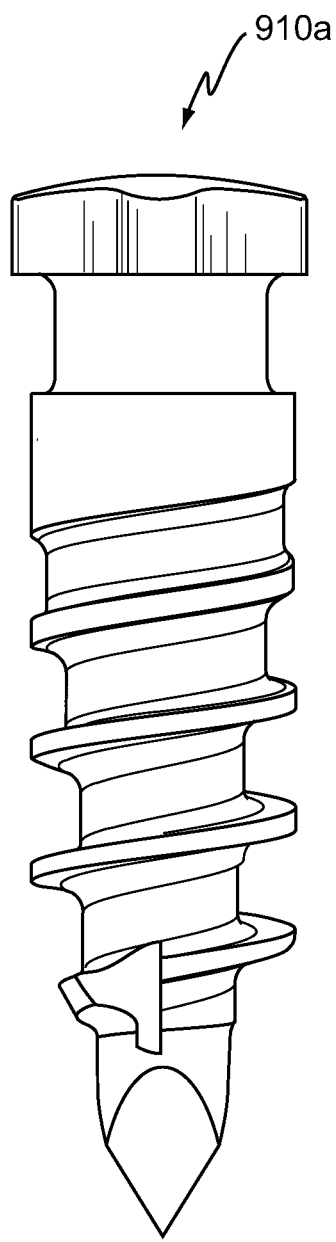
FIG. 10  FIG. 10A

SYSTEM WITH INTEGRAL LOCKING MECHANISM

FIELD OF INVENTION

The present invention is directed to systems for affixing at least two portions of bone.

BACKGROUND

The present disclosure is related to commonly owned and copending U.S. application Ser. No. 12/551,132 and Ser. No. 12/551,182, each of which has a filing date that is the same as the present disclosure, and both of which are hereby incorporated herein by reference in their entireties.

The present disclosure relates to affixing at least two portions of bone, as well as locking mechanisms for the same.

SUMMARY OF THE INVENTION

A system for affixing at least two portions of bone is provided. The system has a first end cap, a second end cap, and a linking member extending between the first end cap and the second end cap, wherein the first end cap has at least one leg configured to connect the linking member to the first end cap and configured to retain said connection.

Additional aspects and features of the present disclosure will be apparent from the detailed description and claims as set forth below.

BRIEF DESCRIPTION OF THE DRAWINGS

FIGS. 10 and 10A are side views of embodiments of fasteners;

DETAILED DESCRIPTION

Figure 1:
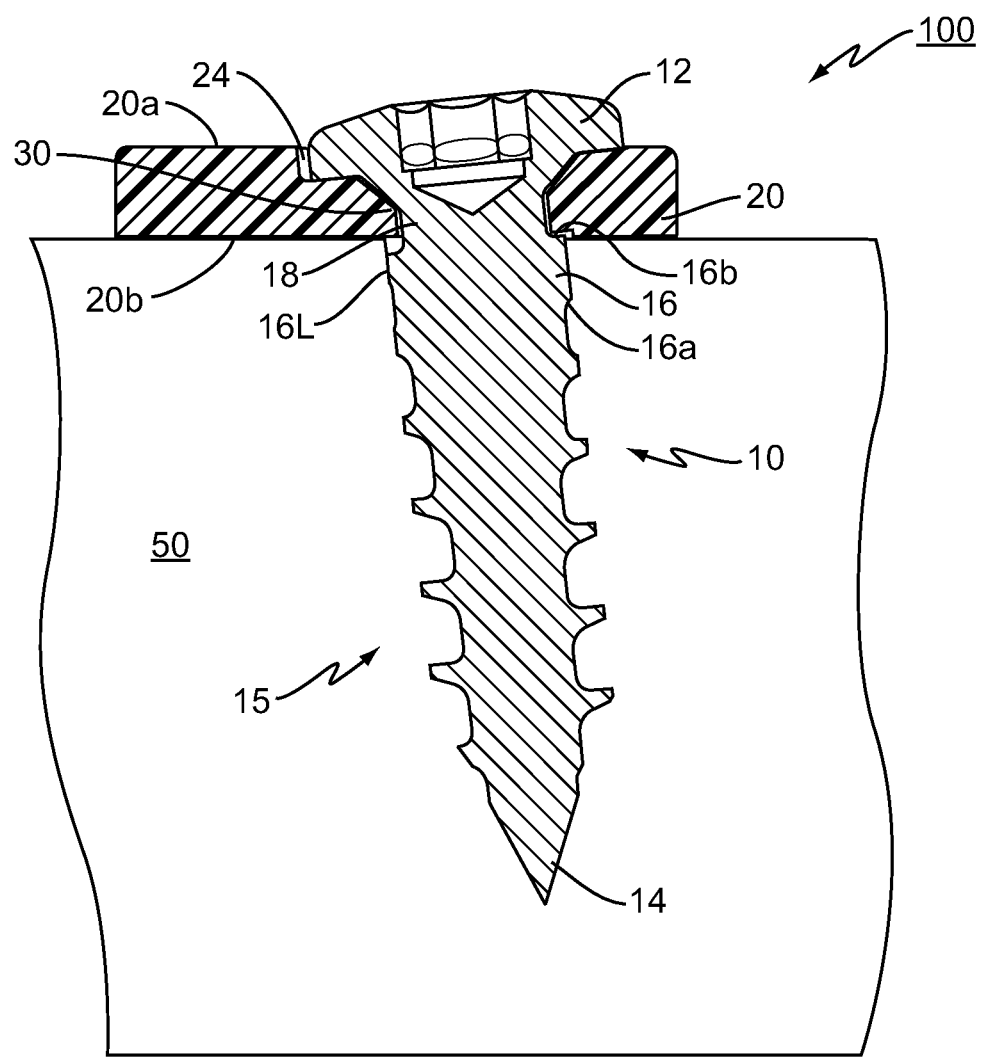
FIG. 1 is a cross-sectional view of a system for affixing a stratum to bone.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 shows a cross-sectional view of a system 100 for affixing a stratum 20 to bone 50. The system 100 has a stratum 20 having a first surface 20a, a second surface 20b, and at least one hole 30 extending between the first surface 20a and the second surface 20b, wherein the second surface 20b is configured to engage at least a portion of the bone 50. The system 100 further has a fastener 10 configured to pass at least partially through the at least one hole 30 and engage at least a portion of the bone 50, wherein the stratum 20 is further configured to deflect, allowing the fastener 10 to pass at least partially through the hole 30. In the context where the stratum 20 may be a spinal plate, for example, the stratum may be used to fuse adjacent vertebrae together in a relatively fixed relationship.

Figure 2:
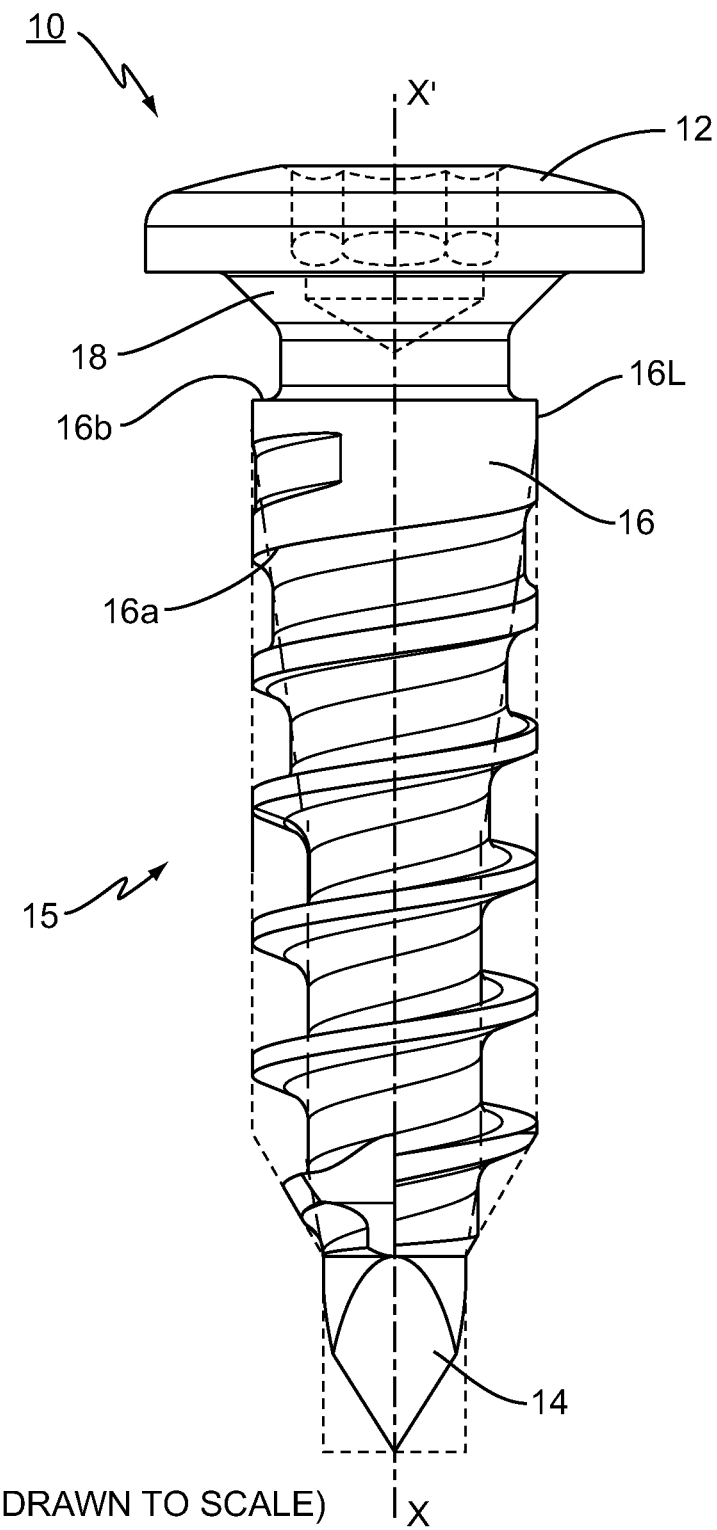
FIG. 2 is a side view of the fastener of the system of FIG. 1.

In the system 100 of FIG. 1, the fastener 10 has a length and a width, the length being greater than the width, and a central longitudinal axis. A side view of the fastener 10 of FIG. 1 is shown in FIG. 2, which is drawn to scale. The fastener 10 further has a head portion 12, an intermediate portion 18, and a distal portion 15. The distal portion 15 has a proximal end 16 that is proximate the intermediate portion 18, and a distal end 14 located at the tip of the fastener 10.

In the context of spinal plates, the fastener 10 may be, for example, a screw. In fact, a screw is shown as the fastener 10 in FIGS. 1 and 2. In an embodiment where the fastener 10 is a screw, the head portion 12 is a head of the screw, the distal portion 15 contains threads of the screw, and the intermediate portion 18 has no threads. The cross section of the fastener 10 may be substantially circular, as is common with screws. As shown in FIGS. 1 and 2, the head portion 12 has a width (or diameter in the case of a fastener having a circular cross section) that is the largest of the fastener 10, while the intermediate portion 18 has the smallest width (or diameter). The distal portion 15 of the fastener 10 has a proximal end 16 having a first width (or diameter) and a distal end 14 having a second width (or diameter), wherein the first width is greater than the second width. As used herein, the width of each respective section is substantially perpendicular to the central longitudinal axis X-X' of the fastener 10.

Figure 1A:
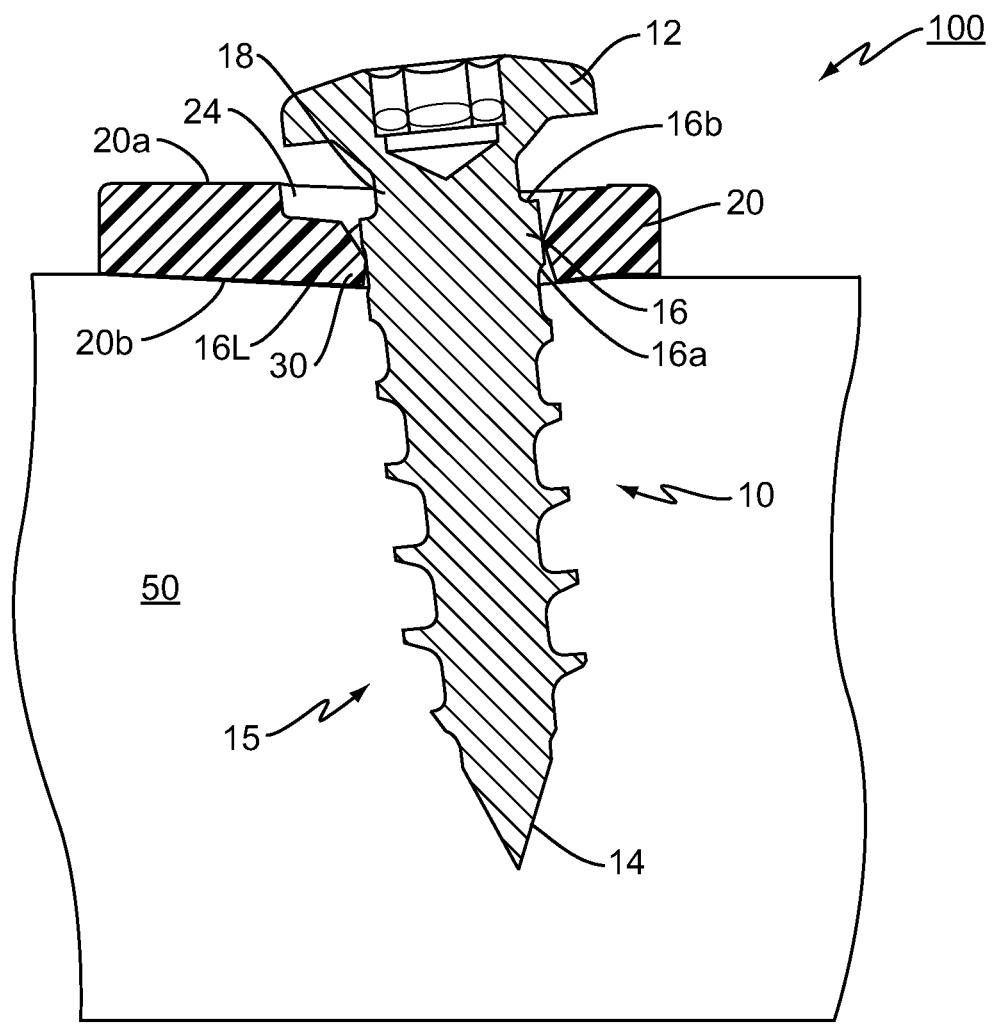
FIG. 1A is a cross-sectional view of the system of FIG. 1, depicting deflection of the stratum.

In the embodiment of FIG. 1, the system 100 shows a stratum 20 that is substantially non-rigid, such as, for example, polyetheretherketone ("PEEK"). Such a stratum may be composed solely of PEEK, or contain enough PEEK so as to be non-rigid. Other suitable non-rigid materials may include, but are not limited to polyetherketoneketone ("PEKK"), ultra high molecular weight polyethylene ("UHMWPE"), polyethylene, shape memory metals and other polymers. The term "substantially" as used herein may be applied to modify any quantitative representation which could permissibly vary without resulting in a change in the basic function to which it is related. For example, a stratum 20 may be considered substantially non-rigid if it can deflect (at the location of the hole 130) upon the insertion of a fastener 10 through hole 30, but rebound to the position or approximate position prior to insertion of the fastener 10. Specifically, system 100 is designed so that the proximal end 16 of the distal portion 15 of the fastener 10 causes the stratum 20 to deflect as the proximal end 16 of the fastener 10 moves across the at least one hole 30 in the stratum 20 in the direction towards the second surface 20b of the stratum 20. FIG. 1A shows system 100 as the proximal end 16 of the fastener 10 moves across the at least one hole 30 in the stratum 20 in the direction towards the second surface 20b of the stratum 20, thereby deflecting the stratum 20.

FIG. 1A illustrates a deflection mechanism that is a type of deflection due to, for example, the characteristics of the material of the stratum 20. In addition to the deflection mechanism illustrated in FIG. 1A, the stratum 20 may deflect in a radial direction so as to enlarge the hole 30. That is, the stratum 20 adjacent to the hole 30 or portions of the stratum 20 adjacent the hole 30 may move in a direction away from the fastener 10, yet remain in the same plane of the stratum 20. In such a mechanism, the stratum 20 deflects in a direction away from and substantially perpendicular to the fastener 10. Such a mechanism is a type of deflection due, for example, the geometry of the stratum 20.

Further, the distal portion 15 of the fastener 10 has a lip 16L that allows passage of the proximal end 16 through the at least one hole 30 in the stratum 20, and prevents inadvertent backing out of the fastener 10, i.e., moving back out of the at least one hole 30 in a direction away from the bone 50. As shown in FIGS. 1, 1A and 2, the lip 16L is situated at the proximal-most location of the distal portion 15 of the fastener 10, and also has the largest width (or diameter) over the distal portion of the fastener 10. Also, when the fastener 10 is inserted through the hole 30 on the stratum 20, the stratum 20 starts to deflect when the surface 16a of the proximal end 16 of the distal portion 15 contacts the stratum 20, whereas the stratum 20 prevents inadvertent backing out of the fastener 10 by means of the contact between the second surface 20b of the stratum 20 and surface 16b of the proximal end 16 of the distal portion 15. In the embodiments of FIGS. 1, 1A and 2, the fastener 10 is made of a material that allows this function to be accomplished. For example, the fastener 10 may be made of a material (metal or non-metal) that is able to cause the stratum 20 to deflect and rebound, as described above. Some suitable materials include, but are not limited to, Titanium Alloys, commercially available Titanium, stainless steel, PEEK, cobalt chrome ("CoCr"), and shape memory metals. Further, as shown in FIG. 1, the stratum 20 has a recess 24 surrounding the hole 30 that helps accommodate at least a portion of the head portion 12 of the fastener 10.

Figure 3:
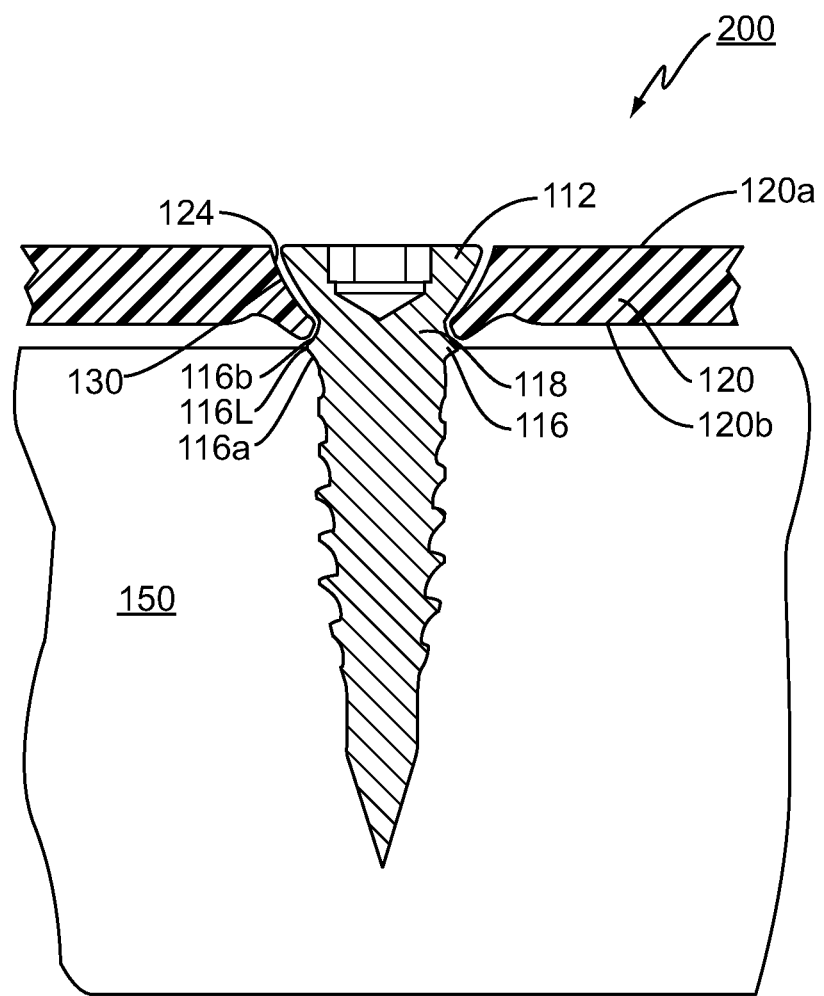
FIG. 3 is a cross-sectional view of another system for affixing a stratum to bone.

FIG. 3 shows a cross-sectional view of a system 200 for affixing a stratum 120 to bone 150. The system 200 has a stratum 120 having a first surface 120a, a second surface 120b, and at least one hole 130 extending between the first surface 120a and the second surface 120b, wherein the second surface 120b is configured to engage at least a portion of the bone 150. The system 200 further has a fastener 110 configured to pass at least partially through the at least one hole 130 and engage at least a portion of the bone 150, wherein the stratum 120 is further configured to deflect, allowing the fastener 110 to pass at least partially through the hole 130.

In system 200 of FIG. 3, the fastener 110 has a length and a width, the length being greater than the width, and a central longitudinal axis. The fastener 110 further has a head portion 112, an intermediate portion 118, and a distal portion 115. The distal portion 115 has a proximal end 116 that is proximate the intermediate portion 118, and a distal end 114 located at the tip of the fastener 110.

In the context of spinal plates, the fastener 110 may be, for example, a screw. In fact, a screw is shown as the fastener 110 in FIG. 3. In an embodiment where the fastener 110 is a screw, the head portion 112 is a head of the screw, the distal portion 115 contains threads of the screw, and the intermediate portion 118 has no threads. The cross section of the fastener 110 may be substantially circular, as is common with screws. As shown in FIG. 3, the head portion 112 has a width (or diameter) that is the largest of the fastener 10, while the intermediate portion 118 has the smallest width (or diameter). The distal portion 115 of the fastener 110 has a proximal end 116 having a first width (or diameter) and a distal end 114 having a second width (or diameter), wherein the first width is greater than the second width. As in the embodiments of FIGS. 1, 1A and 2, as used herein, the width of each respective section is substantially perpendicular to the central longitudinal axis of the fastener 110.

In the embodiment of FIG. 3, the system 100 shows a stratum 120 that is substantially non-rigid, such as, for example, polyetheretherketone ("PEEK"). Such a stratum may be composed solely of PEEK, or contain enough PEEK so as to be non-rigid. Other suitable materials for the stratum 120 of FIG. 3 are similar to those that are suitable for the stratum 20 of FIGS. 1 and 1A. A stratum 120 may be considered substantially non-rigid if can deflect (at the location of the hole 30) upon the insertion of a fastener 110 through hole 130, but rebound to the position or approximate position prior to insertion of the fastener 110. Specifically, system 200 is designed so that the proximal end 116 of the distal portion 115 of the fastener 110 causes the stratum 120 to deflect as the proximal end 116 of the fastener 110 moves across the at least one hole 130 in the stratum 120 in the direction towards the second surface 120b of the stratum 120.

Further, the distal portion 115 of the fastener 110 has a lip 116L that allows passage of the proximal end 116 through the at least one hole 130 in the stratum 120, and prevents inadvertent backing out of the fastener 110, i.e., moving back out of the at least one hole 130 in a direction away from the bone 150. As shown in FIG. 3, the lip 116L is situated at the proximal-most location of the distal portion 115 of the fastener 110, and also has the largest width (or diameter) over the distal portion of the fastener 110. Also, when the fastener 110 is inserted through the hole 130 on the stratum 120, the stratum 120 starts to deflect when the surface 116a of the proximal end 116 of the distal portion 115 contacts the stratum 120, whereas the stratum 120 prevents inadvertent backing out of the fastener 110 by means of the contact between the second surface 120b of the stratum 120 and surface 116b of the proximal end 116 of the distal portion 115. In the embodiment of FIG. 3, as with those illustrated in the previous Figures, the fastener 110 is made of a material that allows this function to be accomplished. For example, the fastener 110 may be made of a material (metal or non-metal) that is able to cause the stratum 120 to deflect and rebound, as described above. As with system 100 of the previous figures, with the system 200 of FIG. 3, the stratum 120 and the lip 116L of the fastener 110 are configured and work in conjunction to allow deflection of the stratum 120 in the direction toward the bone 150, while at the same time, work to not allow deflection in the opposite direction, i.e., to prevent inadvertent backing out of the fastener. Further, as shown in FIG. 3, the stratum 120 has a recess 124 surrounding the hole 130 that helps accommodate at least a portion of the head portion 112 of the fastener 110.

Figure 4:
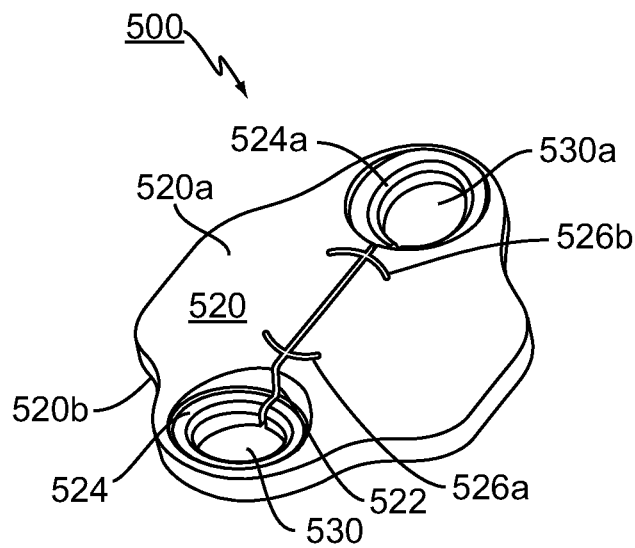
FIG. 4 is an isometric view of a system with integral locking mechanism.

FIG. 4 shows an isometric view of a system 500 with integral locking mechanism. System 500 for affixing a stratum 520 to bone has a stratum 520 having a first surface 520a, a second surface 520b, and at least one hole 530 extending between the first surface 520a and the second surface 520b, wherein the second surface 520b is configured to engage at least a portion of the bone (shown, for example, as bone 50 in FIGS. 1, 1A and 3). The system 500 further has a fastener (shown, for example, as fastener 10 in FIGS. 1, 1A and 2)

configured to pass at least partially through the at least one hole 530 and engage at least a portion of the bone, wherein the stratum 520 is further configured to deflect, allowing the fastener to pass at least partially through the hole 530.

In the context of spinal plates, plates may be used to fuse adjacent vertebrae together in a relatively fixed relationship. In particular, stratum 520 has a first hole 530 and a second hole 530a. For example, each hole may be positioned over different, yet adjacent, vertebral bodies. Stratum 520 further has a slot 522 in the stratum 520 that extends from the at least one hole 530 to another location on the stratum 520. Specifically, slot 522 extends from the first hole 530 to the second hole 530a. The slot 522 facilitates deflection of the stratum 520 that allows the fastener to pass at least partially through the first hole 530, as well as another fastener to pass through the second hole 530a. On stratum 520, the first hole 530 and the second hole 530a further have recesses 524 and 524a, respectively, and the slot 522 intersects the respective recesses 524 and 524a. Stratum 520 further has secondary slots 526a and 526b. As shown on stratum 520, the secondary slots 526a and 526b may be curved or have the shape of an arc. Slots 526a and 526b further facilitate deflection of the stratum 520 that allows the fastener to pass at least partially through the first hole 530, as well as another fastener to pass through the second hole 530a.

In particular, the slots 522, 526a and 526b of system 500 are provided to allow the stratum 520 surrounding holes 530 and 530a to deflect in the radial direction. That is, the slots 522, 526a and 526b provide a geometrical design that allows the holes 530 and 530a to enlarge, increasing their respective radii, when the portions of the stratum 520 adjacent to the holes 530 and 530a move in a direction away from the holes, but remain substantially in the plane of the stratum 520. In doing so, the portions of slot 522 adjacent to the holes 530 and 530a widen as the fastener passes through the holes 530 and 530a. After a fastener is in its intended implanted position, the corresponding slots move back to their original positions, as shown in FIG. 4. In one embodiment of system 500, where stratum 520 has a thickness of 2.0 mm., the hole 530 in such a stratum 520 may have a diameter of 3.4 mm., and the slot 522 extending from such a hole 520 may be 0.25 mm. wide.

Figure 5:
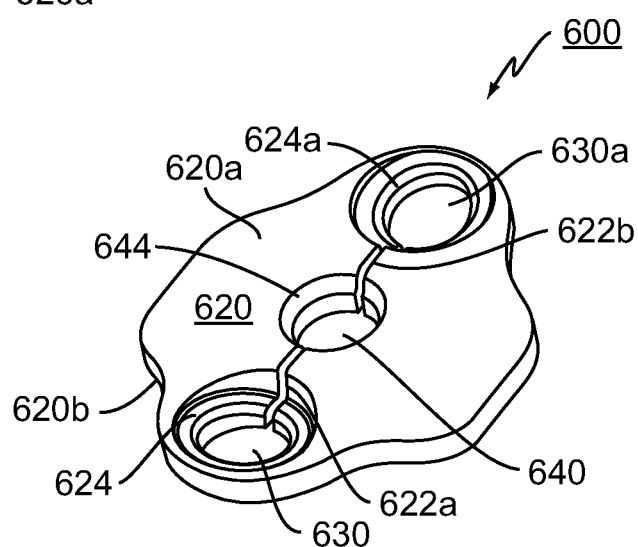
FIG. 5 is an isometric view of another system with integral locking mechanism.

FIG. 5 shows an isometric view of a system 600 with integral locking mechanism. System 600 for affixing a stratum 620 to bone has a stratum 620 having a first surface 620a, a second surface 620b, and at least one hole 630 extending between the first surface 620a and the second surface 620b, wherein the second surface 620b is configured to engage at least a portion of the bone (shown, for example, as bone 50 in FIGS. 1, 1A and 3). The system 600 further has a fastener 610 (shown, for example, as fastener 10 in FIGS. 1, 1A and 2) configured to pass at least partially through the at least one hole 630 and engage at least a portion of the bone, wherein the stratum 620 is further configured to deflect, allowing the fastener to pass at least partially through the hole 630.

In the context of spinal plates, plates may be used to fuse adjacent vertebrae together in a relatively fixed relationship. In particular, stratum 620 has a first hole 630 and a second hole 630a. For example, the first hole 630 and the second hole 630a may be positioned over different, yet adjacent, vertebral bodies. Stratum 620 further has a third hole 640, which may be positioned over a spacer or other intra-discal device located between adjacent vertebrae. Stratum 620 further has a first slot 622a in the stratum 620 that extends from the at least one hole 630 to another location on the stratum 620. Specifically, slot 622a extends from the first hole 630 to the third hole 640. Stratum 620 further has a second slot 622b in the stratum 620 that extends from the second hole 630a to another location on the stratum 620. Specifically, slot 630b extends from the second hole 630a to the third hole 640. The first slot 622a facilitates deflection of the stratum 620 that allows the fastener to pass at least partially through the first hole 630. Similarly, the second slot 622b facilitates deflection of the stratum 620 that allows another fastener to pass through the second hole 630a. On stratum 620, the first hole 630 and the second hole 630a further have recesses 624 and 624a, respectively, which the respective slots 622a and 622b intersect. Further, the slots 622 and 622a each intersect a recess 644 of the third hole 644. Note that the mechanism of deflection of system 600 is similar to that of system 500, i.e., slots 622a and 622b are provided to allow the stratum 620 surrounding holes 630 and 630a to deflect in the radial direction.

Figure 6:
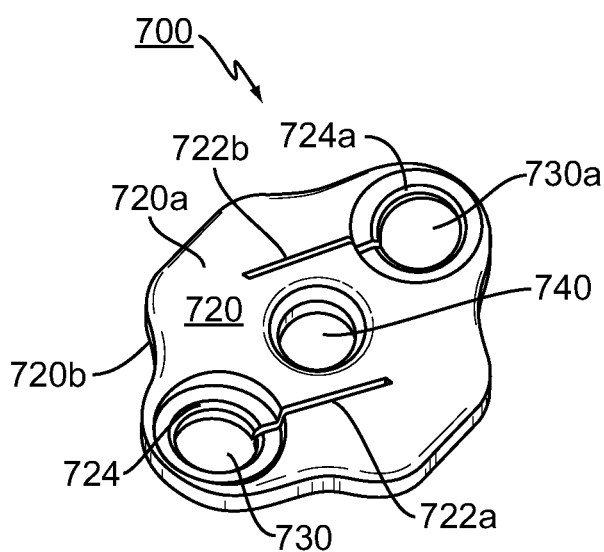
FIG. 6 is an isometric view of another system with integral locking mechanism.

FIG. 6 shows an isometric view of a system 700 with integral locking mechanism. System 700 for affixing a stratum 720 to bone has a stratum 720 having a first surface 720a, a second surface 720b, and at least one hole 730 extending between the first surface 720a and the second surface 720b, wherein the second surface 720b is configured to engage at least a portion of the bone (shown, for example, as bone 50 in FIGS. 1, 1A and 3). The system 700 further has a fastener 710 (shown, for example, as fastener 10 in FIGS. 1, 1A and 2) configured to pass at least partially through the at least one hole 730 and engage at least a portion of the bone, wherein the stratum 720 is further configured to deflect, allowing the fastener to pass at least partially through the hole 730.

In the context of spinal plates, plates may be used to fuse adjacent vertebrae together in a relatively fixed relationship. In particular, stratum 720 has a first hole 730 and a second hole 730a. For example, the first hole 730 and the second hole 730a may be positioned over different, yet adjacent, vertebral bodies. Stratum 720 further has a third hole 740, which may be positioned over a spacer or other intra-discal device located between adjacent vertebrae. Stratum 720 further has a first slot 722a in the stratum 720 that extends from the at least one hole 730 to another location on the stratum 720. Stratum 720 further has a second slot 722b in the stratum 720 that extends from the second hole 730a to another location on the stratum 720, a location that is a different location than the location where the first slot 722a terminates. The first slot 722a facilitates deflection of the stratum 720 that allows the fastener to pass at least partially through the first hole 730. Similarly, the second slot 722b facilitates deflection of the stratum 720 that allows another fastener to pass through the second hole 730a. On stratum 720, the first hole 730 and the second hole 730a further have recesses 724 and 724a, respectively, which the respective slots 722a and 722b intersect. Note that the mechanism of deflection of system 700 is similar to that of systems 500 and 600, i.e., slots 722a and 722b are provided to allow the stratum 720 surrounding holes 730 and 730a to deflect in the radial direction.

Note that any of the slots described above may have different shapes than those shown and described. For example, any of the slots may be linear, curved, or take on a variety of other shapes.

Figure 7:
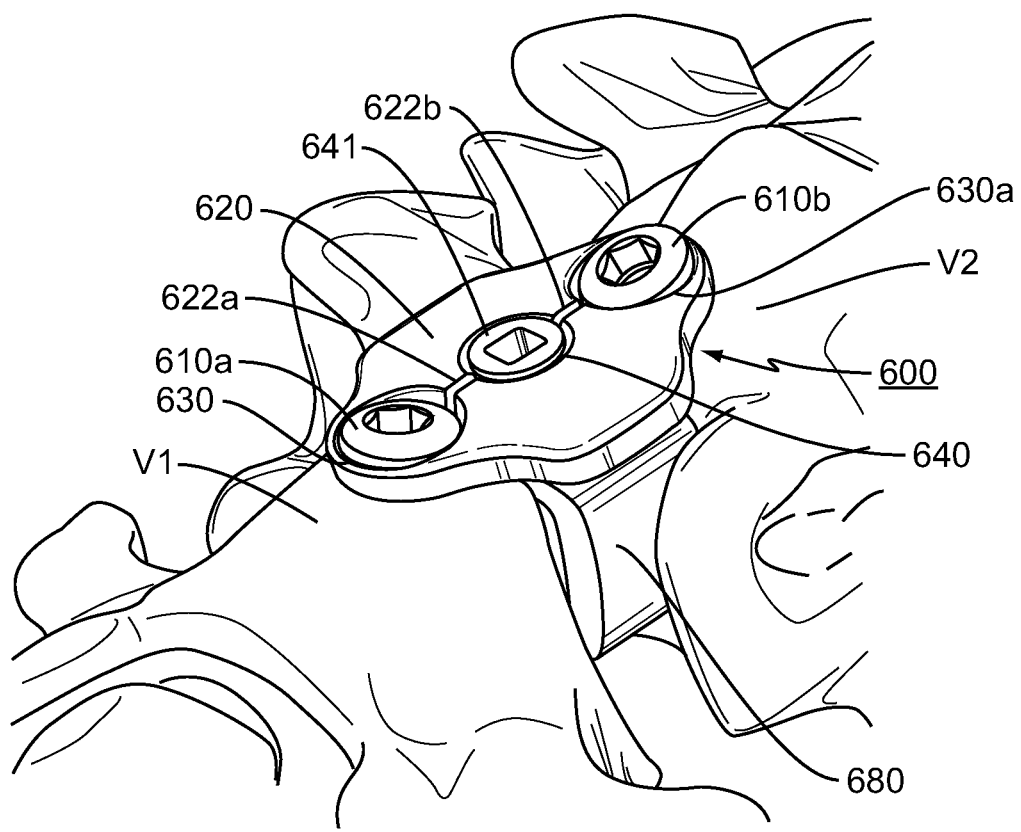
FIG. 7 is the system of FIG. 5 in cooperation with a portion of vertebral column.

FIG. 7 shows an isometric view of system 600 in cooperation with a portion of vertebral column. In particular, FIG. 7 depicts the stratum 620 positioned over two vertebral bodies V1 and V2 and an intradiscal device 680 (such as spacer) that is located in the disc space between the two vertebral bodies V1 and V2. Specifically, the first hole 630 of the stratum 620 is positioned over vertebral body V1, the second hole 630a is positioned over vertebral body V2, and the third hole 640 is positioned over the intradiscal device 680. The stratum is affixed to the vertebral bodies V1 and V2 by means of fasteners 610a and 610b, respectively, which may, for example, be screws (such as screw 10 shown and described with reference to FIGS. 1, 1A, 2 and 3). Specifically, as shown in FIG. 7, fastener 610a is positioned through hole 630, and fastener 610b is positioned through hole 630a. When fastener 610a is placed through the first hole 630 and into the vertebral body V1, the first slot 622a facilitates deflection of the stratum 620. Similarly, the second slot 622b facilitates deflection of the stratum 620 when fastener 610b is placed through the second hole 630a and into the vertebral body V2. Further, a fastener 641 such as a screw may be placed through the third hole 640 and into the intradiscal device 680.

Note that all of the previous systems provide a monolithic stratum having the capability for self locking. That is, in the exemplary context of spinal plates, the systems 100, 200, 500, 600 and 800 provide monolithic plates (or stratums) with integral locking mechanisms that do not require an additional locking element, i.e., something in addition to the stratum, to prevent inadvertent backing out of a fastener.

Figure 8:
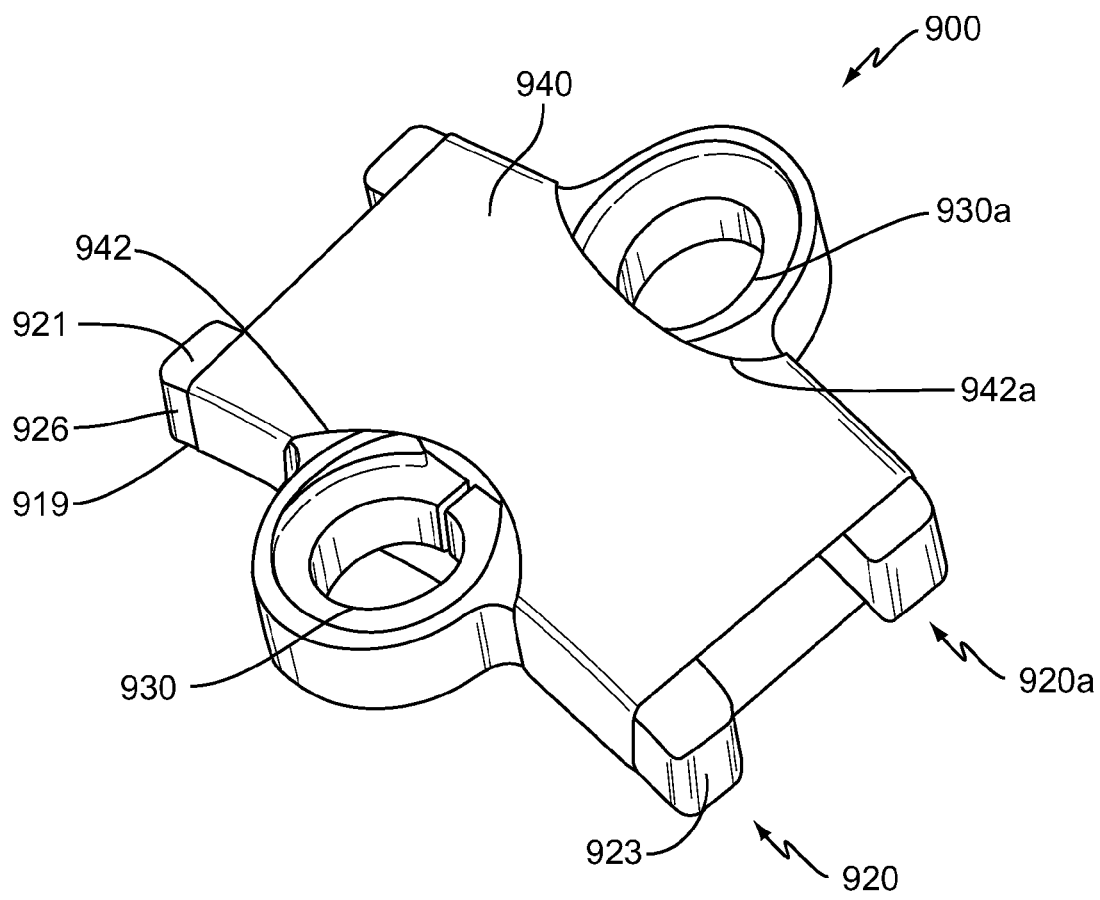
FIG. 8 is an isometric view of another system for affixing at least two portions of bone.

FIG. 8 shows an isometric view of a system 900 for affixing at least two portions of bone, such as, for example two adjacent vertebral bodies V1 and V2. The system 900 has a first end cap 920, a second end cap 920a, and a linking member 940 extending between the first end cap 920 and the second end cap 920a, wherein the first end cap 920 has at least one leg 923 configured to connect the linking member 940 to the first end cap 920 and configured to retain said connection. The first end cap 920 further has a second leg 926 configured to connect the linking member 940 to the first end cap 920 and configured to retain said connection. As shown in FIG. 8, the first end cap 920 further has a first surface 921, a second surface 919, and at least one hole 930 extending between the first surface 921 and the second surface 919, wherein the second surface 919 is configured to engage at least a portion of the bone.

Figure 9:
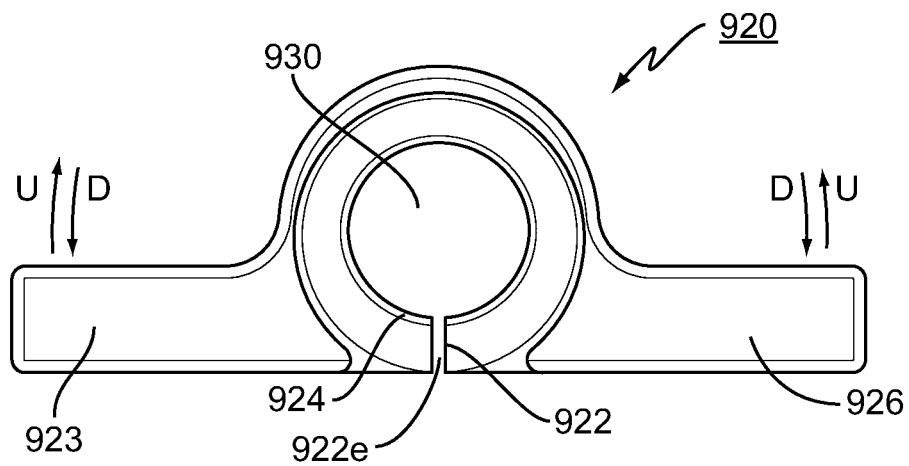
FIG. 9 is a top view of the first end cap of the system of FIG. 8.
Figure 9A:
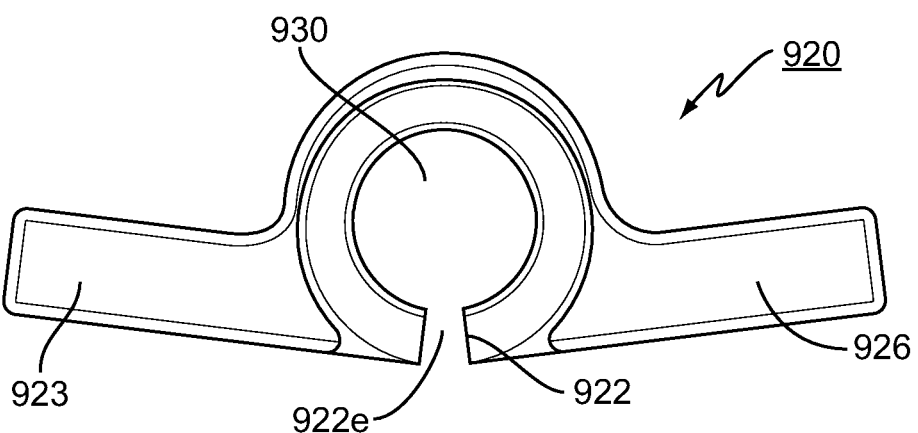
FIG. 9A is an illustrative view of the end cap of FIG. 9.

FIG. 9 shows a top view of the first end cap 920 of the system 900 of FIG. 8. As shown in FIG. 9, the first end cap further has a slot 922 slot that extends from the hole 930 to another location 922e on the first end cap 920 so that a fastener can pass at least partially through the hole 930 and engage at least a portion of the bone, wherein the first end cap 922 is further configured to deflect, allowing the fastener to pass at least partially through the hole. Note that the mechanism of deflection of system 900 is similar to that of systems 500, 600 and 700, i.e., slot 922 is provided to allow the end cap 920 surrounding hole 930 to deflect in the radial direction. In particular, slot 922 allows legs 923 and 926 to separate when a fastener passes through the hole 930 and the slot 922 increases in size (i.e., when legs 923 and 926 move in the direction or a direction similar to that indicated by arrows U in FIG. 9). Further, when the fastener is in its intended implanted position, the end cap 920 prevents inadvertent backing out of the fastener. In addition, the linking member 940 itself, by connecting the first end cap 920 and the second end cap 920a and placed in tension, makes the legs 923 and 926 on end cap 920 move closer together, i.e., constraining the size of slot 922 (i.e., when legs 923 and 926 move in the direction or a direction similar to that indicated by arrows D in FIG. 9). For illustrative purposes, FIG. 9A shows a top view of end cap 920 of system 900 of FIG. 8 when the hole 930 of end cap 920 deflects in the radial direction when the proximal end of the fastener moves across the hole 930 in the direction towards the second surface 919 of the end cap 920. As shown in FIG. 9A, slot 922 has an expanded size. When the slot 922 increases in size, the fastener is able to be inserted through the hole 930, and when the fastener reaches its intended implanted position, the slot 922 has returned to its original size (as shown in FIG. 9) or at least decreased from its expanded size (as shown in FIG. 9A), and linking member 940 helps prevent inadvertent backing out of the fastener. The end cap 920a and its corresponding slot work in the same manner.

In one embodiment of system 900, where end cap 920 has a thickness of 2 mm., the hole 930 in such end cap 920 may have a diameter of 3.4 mm., and the slot 922 extending from such a hole 930 may be 0.25 mm. wide.

FIGS. 10 and 10A show respective side views of two fasteners 910 and 910a, respectively, that can be used with system 900 and end caps 920 and 920a. Fastener 910 is similar to, for example, fastener 10 of FIGS. 1, 1A and 2, in that it can cause the end caps 920 or 920a to deflect when the fastener 910 passes at least partially through hole 930 or 930a, and still help prevent inadvertent backing out of the fastener 910 after it is in its intended implanted position. In this way, fastener 910a is similar to fastener 910, but fastener 910a is a hybrid screw as illustrated and described in copending U.S. application Ser. No. 12/423,951, which is hereby incorporated herein by reference in its entirety.

Figure 11:
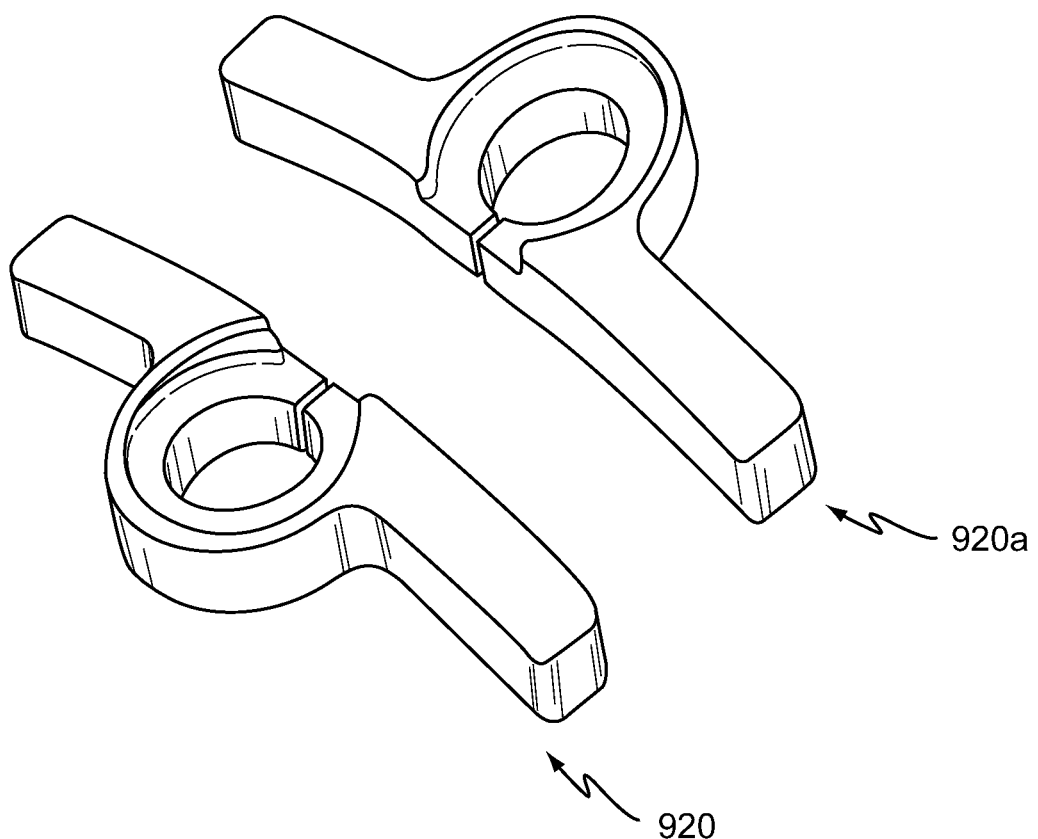
FIG. 11 is an isometric view of the end caps of the system of FIG. 8.
Figure 12:
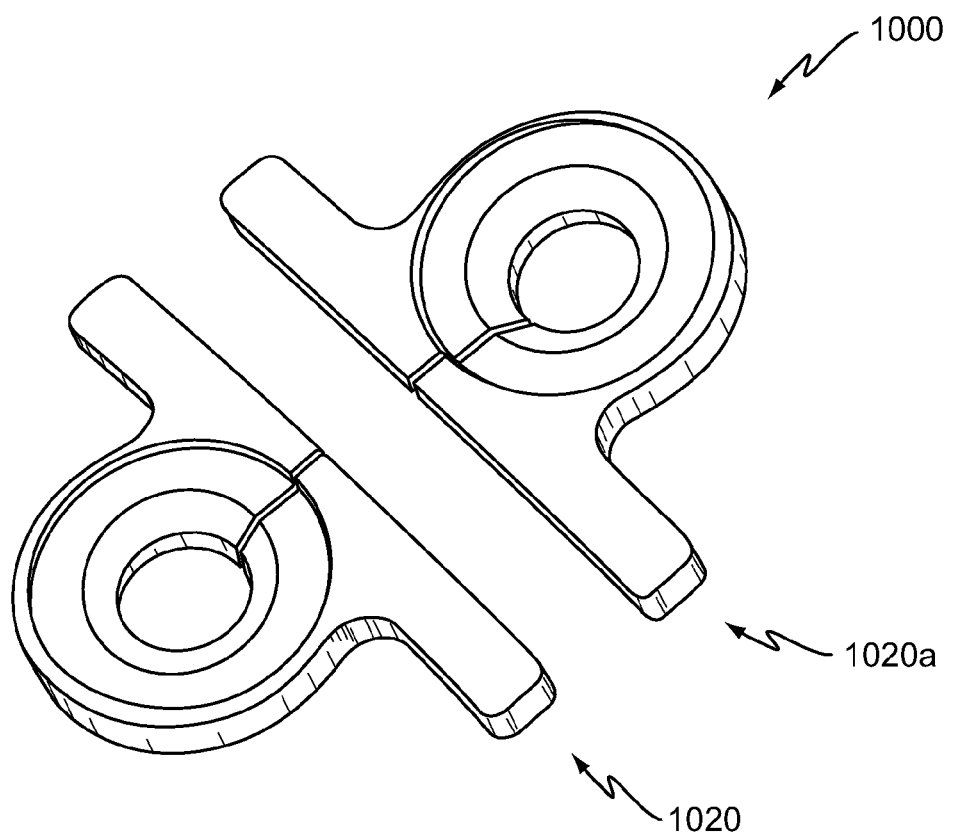
FIG. 12 is an isometric view of the end caps of another system for affixing at least two portions of bone.
Figure 13:
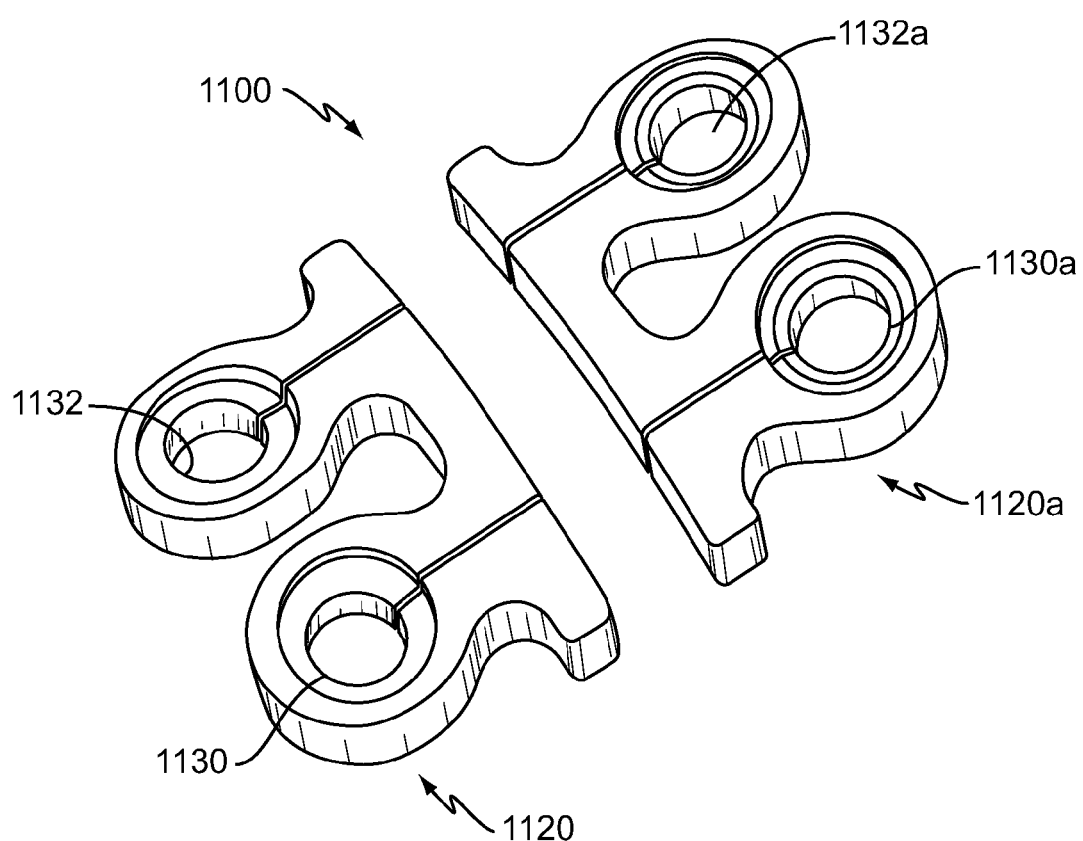
FIG. 13 is an isometric view of the end caps of another system for affixing at least two portions of bone.

FIG. 11 shows an isometric view of end caps 920 and 920a of system 900 of FIG. 8. In particular, for illustrative purposes, FIG. 11 shows the system 900 without the linking member 940. The system 900 of FIGS. 8 and 11 shows an embodiment that may, for example, be used to affix two adjacent vertebrae V1 and V2. FIG. 12 shows end caps 1020 and 1020a of another system 1000. As with FIG. 11, system 1000 is shown without a linking member between end caps 1020 and 1020a. The system 1000 of FIG. 12 shows an embodiment that may be used, for example, to affix two non-adjacent vertebrae, i.e., that spans more than one vertebral level. Similarly, FIG. 13 shows another embodiment 1100 that may be used, for example, to affix two non-adjacent vertebrae, i.e., spanning more than one vertebral level. Specifically, FIG. 13 shows end caps 1120 and 1120a of system 1100. In addition to some dimensional differences from system 1000, the end caps 1120 and 1120a of system 1100 each have two holes 1130, 1132 and 1130a, 1132a, respectively, to receive two fasteners per end cap as opposed to just one. The dimensions of systems 1000 and 1100 may be the same or similar to that of system 900.

Note that, as shown in system 900 of FIG. 8, the linking member 940 connects the end caps 920 and 920a by overlapping the two end caps 920 and 920a. That is, the linking member 940 may be, for example, as shown in FIG. 8, a loop of material that connects the two end caps 920 and 920a. The area on the end caps 920 and 920a that surround the two holes 930 and 930a are positioned in respective holes 942 and 942a in the linking member 940. In this way, the legs (for example, 923 and 926 of end cap 920) of each end cap 920 and 920a are configured to connect the linking member 940 to each end cap 920 and 920a and configured to retain said connections.

Figure 14:
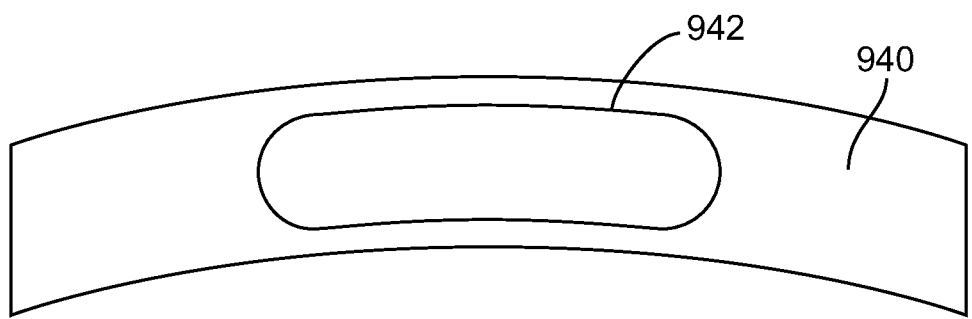
FIG. 14 is a view of the linking member of FIG. 8.

FIG. 14 shows a view of the linking member 940 of FIG. 8, and in particular, a view that depicts hole 942 in linking member 940, but also a view that shows that system 900 may have a curvature so as to engage bone portions that have a corresponding curvature. For example, if used to affix adjacent vertebrae of the cervical portion of one's spine, system 900 may have a concavity in the transverse direction, i.e., a direction substantially perpendicular to the longitudinal axis of the vertebral column. In one embodiment of system 900 of FIG. 8, the system 900 may have a longitudinal length of 19 mm., each end cap 920 and 920a may have a width of 16 mm. and a height of 5.75 mm., the linking member 940 may have a longitudinal length of 15.5 mm., and the thickness of the linking member 940 may be 2.0 mm.

The linking member 940 may be made of an elastic, woven, knitted or braided or flexible material including but not limited to a cloth, polymer, metal, or tissue or combination thereof. The linking member 940 may be formed from a wide variety of suitable materials, including natural or synthetic tissue biocompatible materials. Natural materials include autograft, allograft and xenograft tissues including but not limited to bone and ligaments. Synthetic materials include metallic materials and polymers. The metallic materials can be formed from shape memory alloy, including shape memory materials made from, for example, the nickel-titanium alloy known as Nitinol ("NiTi"). The shape memory materials may exhibit shape memory, but preferably exhibit superelastic behavior. Other metallic materials include titanium alloy, titanium, stainless steel, and cobalt chrome alloy. Suitable polymeric materials include, for example, polyethylene, polyester, polyvinyl, polyvinyl alcohol, polyacrylonitrile, polyamide, polytetrafluoroethylene, poly-paraphenylene, terephthalamide and combinations thereof. Some woven, knitted or braided materials may, for example, include nylon, Dacron®, and/or woven fibers or filaments of polyester, polyethelene, polypropylene, polyetheretherketone ("PEEK"), polytetrafluoroethylene ("PTFE"), woven PEEK, and/or Bionate® or Pursil® manufactured by DMS PTG, Inc. of Berkeley, Calif. Some elastic materials may, for example, include latex, rubber, silicone, polyurethane, silicone-polyurethane copolymers, and/or polyolefin rubbers. Other suitable materials may, for example, include Gore-Tex®, Kevlar®, Spectra, polyether, polycarbonate urethane, shape memory material with pseudo elastic or superelastic characteristics, metals, metal alloys, and polymers, braided polymers, materials made of bone, any bio-compatible material such as an elastomer, demineralized bone, or flexible composite material, ceramic materials, carbon fiber, other natural materials such as allograft, autograft and xenograft, polyacrilonitrile, glass fiber, collagen fiber, ceramic fiber, synthetic resorbable materials such as polyactide, polygycolide, polyorthoester, calcium phosphate, and/or glass, nonresorbable polyethylene, cellulose, materials that are potentially absorbable, and/or materials that are used in making artificial ligaments. One embodiment of the linking member 940 has polyurethane in a woven fabric structure and is coated with BioSpan® S polyurethane, which is manufactured by the Polymer Technology Group of Berkeley, Calif. In addition to woven, braided, or knitted structures, the linking member 940 also may be composed of non-woven structures such as non-woven mesh, or chained structures.

The end caps 920 and 920a of system 900 or any other system herein may be formed from a variety of alternative materials including, by way of non-limiting example, metal or a plastic material such as PEEK. Additional materials that the end caps 920 and 920a could be made of include metals, ceramics and other polymers, and also could include absorbables or adsorbables like Hydrosorb and natural materials like bone, and other tissue—natural or processed—PEK, Polyglycolic Acid, Hydroxyappetite (HA), or a stiffer fabric portion. In one embodiment of system 900, end caps 920 and 920a are made of PEEK and coated with Silicone, except that the portions of end caps 920 and 920a that engage the fasteners are not coated.

The fasteners 910 and 910a of system 900 or any other system herein may be formed from a variety of alternative materials including, by way of non-limiting example, metal or a plastic material such as PEEK. Other suitable materials for the fasteners 910 and 910 include any of those listed above as suitable for fastener 10.

Note that similar to previously described systems, systems 900, 1000 and 1100 provide monolithic end caps having the capability for self locking. That is, in the exemplary context of spinal plates, systems 900, 1000 and 1100 provide monolithic end caps with integral locking mechanisms that do not require an additional locking element, i.e., something in addition to the stratum other than the linking member, to prevent inadvertent backing out of a fastener.

All adjustments and alternatives described above are intended to be included within the scope of the invention, as defined exclusively in the following claims. Those skilled in the art also should realize that such modifications and equivalent constructions or methods do not depart from the spirit and scope of the present disclosure, and that they may make various changes, substitutions, and alterations herein without departing from the spirit and scope of the present disclosure. Furthermore, as used herein, the terms components and modules may be interchanged. It is understood that all spatial references, such as "superior," "inferior," "anterior," "posterior," "outer," "inner," and "perimeter" are for illustrative purposes only and can be varied within the scope of the disclosure.

The invention claimed is:

1. A system for affixing at least two portions of bone, the system comprising:
a linking member extending between a first end including a first opening and a second end including a second opening, the linking member having a first aperture on a first lateral surface and a second aperture on a second lateral surface, opposite the first lateral surface, the linking member having an inner surface defining a passage extending from the first opening to the second opening;
a first end cap extending between a first end and a second end, the first end cap including a first intermediate portion including a first hole, wherein the first end cap is positioned in the passage such that the first intermediate portion extends through the first aperture; and
a second end cap extending between a first end and a second end, the second end cap including a second intermediate portion including a second hole, wherein the second end cap is positioned in the passage such that the second intermediate portion extends through the second aperture,
wherein the linking member is more flexible than the first and second end caps and the first end cap has at least one leg configured to connect the linking member to the first end cap and configured to retain said connection.

2. The system of claim 1, wherein the first end cap has a first leg and a second leg, each leg being positioned within the passage and configured to connect the linking member to the second end cap and configured to retain said connection.

3. The system of claim 2, wherein the second end cap further has a first leg and a second leg, each leg being positioned within the passage and in substantial parallel alignment with the first and second legs of the first cap and configured to connect the linking member to the second end cap and the second end cap and configured to retain said connection between the second end cap and the linking member.

4. The system of claim 3, wherein the first hole is configured for receiving a first fastener, and the second hole is configured for receiving a second fastener.

5. The system of claim 2, wherein the linking member resiliently biases the first and second legs of the first and second end caps inwardly so as to resist inadvertent backing out of bone fasteners from the first and second holes.

6. The system of claim 5, wherein the linking member comprises a loop of material surrounding the first and second legs of the first and second end caps.

7. The system of claim 1, wherein the linking member comprises a material selected from woven, knitted, braided, nonwoven mesh, or chained structures.

8. The system of claim 1, wherein the first end cap and the second end cap each comprise polyetheretherketone.

9. The system of claim 1, wherein the linking member comprises a shape memory material that exhibits superelastic behavior.

10. The system of claim 1, wherein the linking member comprises polyetheretherketone.

11. The system of claim 1, wherein the first and second end caps are monolithically formed and discrete from one another.

12. A system for affixing at least two portions of bone, the system comprising:
a linking member extending between a first end including a first opening and a second end including a second opening, the linking member having a first aperture on a first lateral surface and a second aperture on a second lateral surface, opposite the first lateral surface, the linking member having an inner surface defining a passage extending from the first opening to the second opening;
a first end cap having a first surface and an opposite second surface configured to engage at least a portion of the bone, the first end cap including a first intermediate portion having a first hole, the first end cap being positioned in the passage such that the first intermediate portion extends through the first aperture; and
a second end cap having a first surface and an opposite second surface configured to engage the bone, the second end cap including a second intermediate portion having a second hole, the second end cap being positioned in the passage such that the second intermediate portion extends through the second aperture,
wherein the first end cap has a first leg and a second leg, each leg being positioned within the passage and configured to connect the linking member to the first end cap and configured to retain said connection between the linking member and the first end cap; and
wherein the second end cap has a first leg and a second leg, each leg being positioned within the passage and configured to connect the linking member to the second end cap and configured to retain said connection between the linking member and the second end cap.

13. The system of claim 12, wherein the first hole is configured for receiving a first fastener, and wherein the second hole is configured for receiving a second fastener.

14. The system of claim 13, wherein the first end cap has only one hole and wherein the second end cap has only one hole.

15. The system of claim 14, wherein the linking member comprises a shape memory material that exhibits superelastic behavior.

16. The system of claim 13, wherein the first end cap and the second end cap each comprise polyetheretherketone.

17. The system of claim 13, wherein the first end cap and the second end cap each comprise rigid material.

18. The system of claim 13, wherein the linking member comprises a material selected from woven, knitted, braided, non-woven mesh, or chained structures.

19. A system for affixing at least two portions of bone, the system comprising:
a linking member extending between a first end including a first opening and a second end including a second opening, the linking member having a first aperture on a first lateral surface and a second aperture on a second lateral surface, opposite the first lateral surface, the linking member having an inner surface defining a passage extending from the first opening to the second opening;
a first end cap including a first intermediate portion including a first hole, the first end cap including a first slot extending through the first intermediate portion and into the first hole, the first end cap being positioned in the passage such that the first intermediate portion extends through the first aperture;
a second end cap including a second intermediate portion having a second hole, the second end cap including a second slot extending through the second intermediate portion and into the second hole, the second end cap being positioned in the passage such that the second intermediate portion extends through the second aperture and the first slot faces the second slot,
wherein the linking member is more flexible than the first and second end caps; the first end cap further has at least one leg configured to connect the linking member to the first end cap, and a second leg configured to retain said connection, the first and second legs being positioned within the passage, the first and second slots being configured to allow the first and second end caps to deflect as a first fastener is inserted into the first hole and a second fastener is inserted into the second hole such that a width of the first and second holes increases.

20. The system of claim 19, wherein the second end cap has a first leg and a second leg, each leg being positioned within the passage and configured to connect the linking member to the second end cap and configured to retain said connection between the linking member and the second end cap.

* * * * *